United States Patent
Franceschi et al.

(10) Patent No.: US 11,759,141 B2
(45) Date of Patent: Sep. 19, 2023

(54) MONITORING DIAPHRAGMATIC RESPONSE TO PHRENIC NERVE STIMULATION

(71) Applicant: CIRCLE SAFE, Aubagne (FR)

(72) Inventors: Frédéric Franceschi, Aubagne (FR); Bertrand Thiery, Aubagne (FR)

(73) Assignee: CIRCLE SAFE, Aubagne (FR)

( * ) Notice: Subject to any disclaimer, the term of this patent is extended or adjusted under 35 U.S.C. 154(b) by 0 days.

(21) Appl. No.: 17/813,731

(22) Filed: Jul. 20, 2022

(65) Prior Publication Data

US 2023/0026175 A1    Jan. 26, 2023

(30) Foreign Application Priority Data

Jul. 20, 2021   (EP) ..................... 21306024

(51) Int. Cl.
*A61B 5/366* (2021.01)
*A61B 5/388* (2021.01)
*A61B 5/00* (2006.01)

(52) U.S. Cl.
CPC .............. *A61B 5/388* (2021.01); *A61B 5/366* (2021.01); *A61B 5/746* (2013.01)

(58) Field of Classification Search
CPC ................................ A61B 5/366; A61B 5/388
USPC ........................................................ 600/301
See application file for complete search history.

(56) References Cited

U.S. PATENT DOCUMENTS 10,064,564 B2    9/2018 Kowalski et al.
2005/0197675 A1*    9/2005 David ................. A61B 5/412 607/9
2015/0057563 A1*    2/2015 Kowalski ............. A61B 5/389 600/554

OTHER PUBLICATIONS

Anwar, O. et al., "Contemporary analysis of phrenic nerve injuries following cryoballoon-based pulmonary vein isolation: A single-centre experience with the systematic use of compound motor action potential monitoring," PLOS ONE, vol. 15, No. 6, Jun. 25, 2020, 11 pages.

(Continued)

*Primary Examiner* — Nicole F Lavert
*Assistant Examiner* — Nicole F Johnson
(74) *Attorney, Agent, or Firm* — Alleman Hall Creasman & Tuttle LLP

(57) ABSTRACT

The disclosure relates to a computer-implemented method for monitoring diaphragmatic response to phrenic nerve stimulation. The method comprises receiving in real-time a diaphragmatic CMAP signal. The method comprises computing a baseline value of a characteristic of the CMAP signal. The characteristic represents a diaphragmatic response intensity to a phrenic nerve stimulation. The method comprises determining a threshold value of the characteristic, representing a boundary of values of the characteristic indicative of upcoming diaphragmatic palsy. The determining of the threshold value includes shifting the baseline value. The method comprises receiving in real-time a ECG signal. The method comprises repeating in real-time: detecting a QRS complex in the ECG signal, monitoring the CMAP signal, computing a real-time value of the characteristic, comparing the real-time value to the threshold value, and outputting an alert when the threshold is passed. The real-time value of the characteristic is asynchronous to the QRS complex.

15 Claims, 6 Drawing Sheets

(56) References Cited

OTHER PUBLICATIONS

European Patent Office, Extended European Search Report Issued in Application No. 21306024.7, dated Jan. 7, 2022, Germany, 11 pages.

Franceschi, F. et al., "Diaphragmatic electromyography during cryoballoon ablation: a novel concept in the prevention of phrenic nerve palsy," Heart Rhythm, vol. 8, No. 6, Jun. 2011, 7 pages.

Franceschi, F. et al., "Electromyographic Monitoring for Prevention of Phrenic Nerve Palsy in Second-Generation Cryoballoon Procedures," Circulation: Arrhythmia and Electrophysiology, vol. 8, No. 2, Apr. 2015, 6 pages.

Franceschi, F. et al., "Novel Electromyographic Monitoring Technique for Prevention of Right Phrenic Nerve Palsy During Cryoballoon Ablation," Circulation: Arrhythmia and Electrophysiology, vol. 6, No. 6, Oct. 10, 2013, 7 pages.

Franceschi, F. et al., "Phrenic nerve monitoring with diaphragmatic electromyography during cryoballoon ablation for atrial fibrillation: The first human application," Heart Rhythm, vol. 8, No. 7, Jul. 2011, 4 pages.

Okishige, K. et al., "Novel method for earlier detection of phrenic nerve injury during cryoballoon applications for electrical isolation of pulmonary veins in patients with atrial fibrillation," Heart Rhythm, vol. 13, No. 9, Sep. 2016, 7 pages.

Sharma, P. et al., "Factors Influencing Diaphragmatic Compound Motor Action Potentials During Cryoballoon Ablation for Atrial Fibrillation," Journal of Cardiovascular Electrophysiology, vol. 27, No. 12, Dec. 2016, 6 pages.

Tovmassian, L. et al., "Diaphragmatic CMAP Monitoring During Cryoballoon Procedures: Surface vs. Hepatic Recording Comparison and Limitations of This Approach," Frontiers in Cardiovascular Medicine, vol. 9, Feb. 8, 2022, 7 pages.

\* cited by examiner

MONITORING DIAPHRAGMATIC RESPONSE TO PHRENIC NERVE STIMULATION

TECHNICAL FIELD

The disclosure relates to methods, a control unit, a system and a computer program for monitoring diaphragmatic response to phrenic nerve stimulation and/or for phrenic nerve stimulation and/or for cryoablation.

BACKGROUND

Atrial fibrillation is a common arrhythmia. One of the treatments offered is ablation of atrial fibrillation with a minimally invasive procedure. Atrial fibrillation ablation is a type of cardiac ablation, which works by scarring or destroying tissue in the heart to disrupt faulty electrical signals causing the arrhythmia. All four pulmonary veins may be isolated for treating the atrial fibrillation by creating a circumferential lesion, e.g. surrounding their ostia. Among minimally invasive cardiac ablation techniques, cardiac cryoablation is a procedure gaining popularity among electrophysiology practitioners. Cryoablation techniques consist in electrical isolation of the pulmonary veins of the heart by cold "burning" of the tissues with a cryoablation catheter, most often a cryoballoon catheter (i.e. cryogenic balloon catheter).

The most common complication of cryoablation techniques is right diaphragmatic palsy (also referred to as "phrenic nerve palsy") caused by injury of the right phrenic nerve, due to the close proximity between the right phrenic nerve and the pulmonary veins, and due to the fact that the rest of the cryoballoon at the entry of a vein deforms said entry and brings it closer to the phrenic nerve. Although such injury does not systematically occur during cryoablation procedures, it still affects a non-negligible number of patients. And even though the injury is most often reversible, a relatively significant part of the concerned patients is still affected on the next day, and for some patients the diaphragmatic palsy may last over a relatively long period of time before self-cure and at time forever.

The research article "*Contemporary analysis of phrenic nerve injuries following cryoballoon-based pulmonary vein isolation: A single-centre experience with the systematic use of compound motor action potential monitoring*", Anwar, O. et. al., 2020, provides an overview of injury of the right phrenic nerve due to cryoablation, as well as techniques for reducing such injury and issues related to such techniques. One technique widely spread and reviewed in this paper is to perform an electric stimulation of the right phrenic nerve at the level of the superior vena cava during the cryoablation procedure. As the phrenic nerve controls muscle contraction of the right diaphragmatic dome, the technique causes a vigorous contraction of the right diaphragmatic dome, and the technique further comprises monitoring the contraction response induced by the electrical stimulation and act thereupon.

FIG. 1 illustrates the conventional manner in the prior art to perform such a phrenic nerve stimulation technique. The figure shows an example of an anatomical section H of the heart on the left side and a corresponding medical image I on the right side, exemplifying the positioning of an electrophysiology catheter 10 for electrical stimulation of the right phrenic nerve PN. Stimulation catheter 10 is introduced through the femoral vein and positioned with its distal end 14 inside the superior vena cava VC to stimulate the phrenic nerve PN. Stimulation catheter 10 comprises at its distal end 14 several (e.g. four) electrodes 11 which are positioned inside the superior vena cava (above the heart), to be as close as possible and facing the phrenic nerve PN. Stimulation catheter 10 may be a straight quadrupolar catheter, a commercially available catheter commonly used. The operator places the electrodes 11 to stimulate the phrenic nerve by operating in a bipolar mode two electrodes. The operator observes the right diaphragmatic contraction caused by the electrical stimulation, which helps the operator to make assessments on possible injury of the right phrenic nerve. Such assessments allow the operator to make clinical decisions to reduce possibilities of complications.

Current solutions to assess the muscular response to the phrenic nerve stimulation are mostly based on abdominal palpation by an operator (e.g. a medical professional). When the operator perceives a decrease of the vigor of the diaphragmatic contraction, or when the contraction vanishes, it means that the phrenic nerve has been injured, and the cryoablation is stopped in emergency. These solutions are thus subjective and relatively inaccurate. Furthermore, they do not allow to avoid right diaphragmatic palsy, but rather establish a diagnostic that a palsy has occurred.

Other solutions include monitoring by a dedicated system a diaphragmatic compound motor action potential (CMAP) signal of a human patient in response to the phrenic nerve stimulation. This allows performing objective analysis of the signal and reacting to unusual situations. However, these solutions as they exist also appear to lack accuracy.

Within this context, there is still a need for an improved solution for monitoring diaphragmatic response to phrenic nerve stimulation, notably during cryoablation.

SUMMARY

It is therefore provided a computer-implemented method for monitoring diaphragmatic response to phrenic nerve stimulation. The method comprises receiving in real-time a diaphragmatic compound motor action potential (CMAP) signal of a human patient. The method further comprises receiving in real-time data (e.g. physiological data) related to the cardiac activity of the human patient. The method also comprises, in real-time, analyzing the CMAP signal. The method is based on the data related to the cardiac activity (e.g. the analysis is based on said data), in a manner such that the analysis of the CMAP signal is not or little affected by potential interferences due to the cardiac activity of the patient.

The data related to the cardiac activity may be an ECG signal of the patient.

The method may comprise detecting a QRS complex in the ECG signal and the method may take into account said detected QRS complex in a manner such that the analysis of the CMAP signal is not or little affected by potential interferences due to detected QRS complex.

The method may comprise providing an output allowing to assess and/or prevent upcoming diaphragmatic palsy. For example, the output may comprise any one or any combination of the following:

an alert, for example a visual alert and/or a sound alert, indicative of upcoming diaphragmatic palsy; and/or a display of data related to the CMAP signal, for example a display of a curve related to the CMAP signal (e.g. a curve of the CMAP signal itself or a curve of a real-time value of a characteristic of the CMAP signal), with optionally a display (e.g. on the same screen than the one displaying the curve, for example in a superimposed manner) of a baseline value of the CMAP signal or of a value of a characteristic thereof (e.g. in the form of a curve or of a single displayed value) and/or a display (e.g. on the same screen than the one displaying the curve, for example in a superimposed manner) of a threshold value of the CMAP signal or of a characteristic thereof (e.g. in the form of a curve or of a single displayed value); and/or a signal commanding a tool (e.g. a pedal or foot switch) at the disposal of a practitioner performing a cryoablation, the signal optionally commanding an alert mechanism of the tool (e.g. causing the tool to vibrate) to alert the practitioner that the cryoablation is to be stopped, and/or a signal commanding automatic stop of the cryoablation (e.g. by switching off a circuit).

The analysis of the CMAP signal may further comprise, in real-time, detecting passing of a threshold associated with the CMAP signal. For example, the output may be provided when the threshold is passed, passing the threshold being indicative of a risk of upcoming diaphragmatic palsy. The threshold may correspond to a shift of a baseline value associated with the CMAP signal.

According to one aspect, the method comprises receiving in real-time a diaphragmatic compound motor action potential (CMAP) signal of the human patient. The method further comprises computing a baseline value of a characteristic of the CMAP signal. The characteristic represents a diaphragmatic response intensity to phrenic nerve stimulation. The method further comprises determining a threshold value of the characteristic. The threshold value represents a boundary of values of the characteristic indicative of upcoming diaphragmatic palsy. The determining of the threshold value includes shifting the baseline value. The method further comprises receiving in real-time an electrocardiogram (ECG) signal of the human patient. The method further comprises, repeating in real-time: detecting a QRS complex in the ECG signal, monitoring the CMAP signal, computing a real-time value of the characteristic, comparing the real-time value to the threshold value, and outputting an alert when the threshold is passed. The real-time value of the characteristic is asynchronous to the QRS complex.

The method may comprise one or more of the following:
the method comprises discarding diaphragmatic responses synchronous to detected QRS complexes;
the method further comprises commanding phrenic nerve stimulation, the method comprising triggering an occurrence of the phrenic nerve stimulation a predetermined amount of time after detection of an occurrence of the QRS complex such that a diaphragmatic response to the triggered occurrence of the phrenic nerve stimulation occurs and ends before a next occurrence of the QRS complex;
the real-time value of the characteristic is an average of the characteristic for several occurrences of the phrenic nerve stimulation;
the real-time value of the characteristic is an average of the characteristic for a predetermined number of consecutive occurrences of the phrenic nerve stimulation;
the predetermined number is below or equal to 5;
the computing of the real-time value of the characteristic comprises calculating one or more CMAP measures performed each on a portion of the CMAP signal beginning at a predetermined amount of time after an occurrence of the phrenic nerve stimulation and lasting for a predetermined time duration after the occurrence of the phrenic nerve stimulation;
the predetermined amount of time is larger than 3 ms and/or lower than 50 ms;
the predetermined time duration is larger than 50 ms and/or lower than 150 ms;
the characteristic is an amplitude difference between two consecutives peaks of the CMAP signal; the characteristic is an area between an isoelectric line and a portion of a curve representing two consecutives peaks of the CMAP signal;
the threshold value corresponds to a drop of the baseline value which is larger than 25% and/or lower than 35%; and/or
the CMAP signal is received from one or more surface electrodes and/or one or more intravascular electrodes.

It is further provided a computer program comprising instructions for performing the method for monitoring diaphragmatic response to phrenic nerve stimulation.

It is further provided a computer readable storage medium having recorded thereon the computer program.

It is further provided a control unit comprising a processor coupled to a memory, the memory having recorded thereon the computer program.

It is further provided an apparatus that comprises the control unit and a housing containing the control unit. The apparatus may further comprise a first electrical interface to connect a first plurality of electrodes configured to measure the CMAP signal, and a second electrical interface to connect a second plurality of electrodes configured to measure the ECG signal.

It is further provided a system. The system comprises the control unit or the apparatus, a first plurality of electrodes configured to measure the CMAP signal, a second plurality of electrodes configured to measure the ECG signal, a phrenic nerve stimulation system, and/or a cryoablation catheter.

The system may comprise one or more of the following:
the first plurality of electrodes comprises one or more surface electrodes and/or one or more intravascular electrodes;
the system further comprises a display for outputting a visual alert when the threshold is passed; and/or
the system further comprises a sound emitting device for outputting a sound alert when the threshold is passed.

It is further provided a method of phrenic nerve stimulation. The method of phrenic nerve stimulation comprises performing phrenic nerve stimulation. The method of phrenic nerve stimulation further comprises, while performing the phrenic nerve stimulation, monitoring a diaphragmatic response to the phrenic nerve stimulation by executing the method for monitoring diaphragmatic response to phrenic nerve stimulation.

It is further provided a method of cryoablation. The method of cryoablation comprises introducing a cryoablation catheter inside a left atrium of a human patient. The method of cryoablation further comprises performing cryoablation. The method of cryoablation further comprises, while performing cryoablation, repeating the method of phrenic nerve stimulation. The method of cryoablation may further comprise, when an alert is outputted as the threshold is passed, pausing the cryoablation, and then resuming the cryoablation.

BRIEF DESCRIPTION OF THE DRAWINGS

Non-limiting examples will now be described in reference to the accompanying drawings, where.

DETAILED DESCRIPTION

Figure 1:
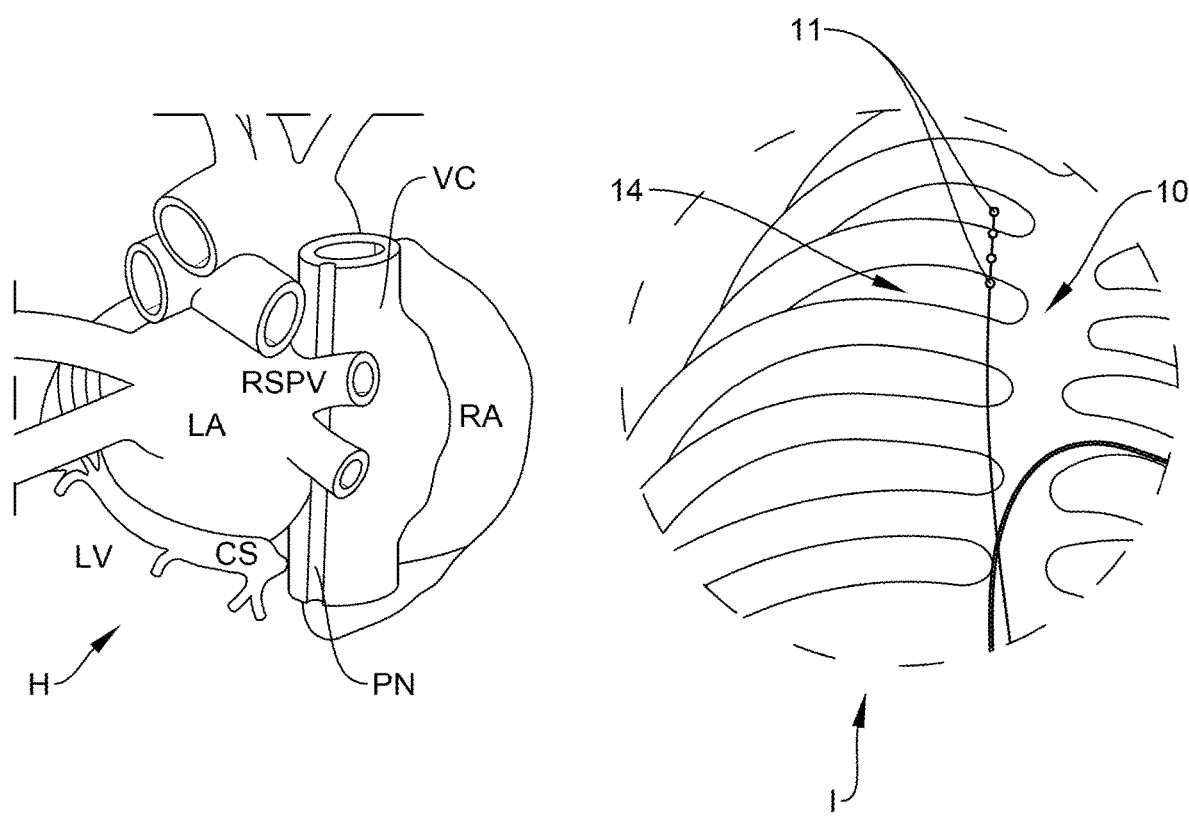
FIG. 1 illustrates the conventional manner in the prior art to perform a phrenic nerve stimulation technique.

As previously discussed, it is proposed a computer-implemented method for monitoring diaphragmatic response to phrenic nerve stimulation is proposed which comprises receiving in real-time a diaphragmatic compound motor action potential (CMAP) signal of a human patient. The method further comprises computing a baseline value of a characteristic of the CMAP signal. The characteristic represents a diaphragmatic response intensity to phrenic nerve stimulation. The method further comprises determining a threshold value of the characteristic. The threshold value represents a boundary of values of the characteristic indicative of upcoming diaphragmatic palsy. The determining of the threshold value includes shifting the baseline value. The method further comprises receiving in real-time an electrocardiogram (ECG) signal of the human patient. The method further comprises repeating in real-time: detecting a QRS complex in the ECG signal, monitoring the CMAP signal, computing a real-time value of the characteristic, comparing the real-time value to the threshold value, and outputting an alert when the threshold is passed. The real-time value of the characteristic is asynchronous to the QRS complex. Such monitoring method forms an improved solution for monitoring diaphragmatic response to phrenic nerve stimulation.

Notably, the monitoring method allows to monitor diaphragmatic response to phrenic nerve stimulation in an objective manner, based on a computed objective real-time value of a characteristic of the CMAP signal. The monitoring method thus allows the objective observation of diaphragmatic response to phrenic nerve stimulation, for example during cryoablation. For that the monitoring method includes receiving in real-time a CMAP signal and an ECG signal of a human patient. The monitoring method also computes a baseline value of a characteristic of the CMAP signal, the characteristic representing a diaphragmatic response intensity to phrenic nerve stimulation. The monitoring method also determines, by shifting the baseline value, a threshold value of the characteristic, that represents a boundary of the characteristic's values indicative of upcoming diaphragmatic palsy. Now, the monitoring method, in real-time, repeatedly and continuously (e.g. at regular time intervals) computes (e.g. automatically) a real-time value of the characteristic and compares it (e.g. automatically) to the threshold value. Thereby the monitoring method objectively computes in real-time an objective value representing the CMAP and detects in real-time when the threshold is passed (i.e. by the computed real-time value of the characteristic), and outputs (e.g. automatically) an alert when this is the case. In other words, the monitoring method is able to output in real-time an alert (e.g. a visual and/or sound alert) indicating that the real-time value of the characteristic passes the threshold, thereby objectively indicating an upcoming diaphragmatic palsy. During cryoablation, the output of the alert allows to pause the cryoablation to avoid injury to the phrenic nerve, and then, resuming the cryoablation (i.e. later, for example when the diaphragmatic response comes back to normal and/or when the alert stops). The monitoring method thus provides a real-time automated and objective assistance (e.g. in the form of a real-time diaphragmatic electromyography) to a surgeon performing cryoablation warning him/her in real-time of a risk of upcoming diaphragmatic palsy. The surgeon may thereby be focused on the cryoablation without having to verify by himself/herself the possible occurrence of a diaphragmatic palsy via palpation, as the monitoring method does that automatically via analysis of a CMAP signal and outputs a real-time alert when palsy may occur. In other words, the monitoring method constitutes an objective and early method of detection and prevention of diaphragmatic palsy.

Furthermore, the real-time value of the characteristic, that the monitoring method computes, is asynchronous to a QRS complex that the method detects in real-time in the ECG signal. In other words, the monitoring method monitors in real time the CMAP signal and uses it to compute the real-time value of the characteristic in such a way that the real-time value is asynchronous to the detected QRS complex in the ECG signal. In yet other words, the monitoring method computes the real-time value of the characteristics using only portions of the CMAP signal that correspond to the diaphragmatic response to phrenic nerve stimulations and that are not synchronous to any portion of the ECG signal that corresponds to a QRS complex occurrence. Thereby, the monitoring method allows to avoid interference of the QRS complex that corresponds to the cardiac electrical activity in the computation of the real-time value of the characteristic. The monitoring method thereby forms an improved solution to monitor diaphragmatic response to phrenic nerve stimulation in that the method provides an accurate real-time measure of the diaphragmatic response (i.e. the characteristic) which is not perturbated by interferences of the QRS complex of the ECG signal. This accuracy improves the real-time monitoring of the diaphragmatic response, notably during cryoablation where the surgeon performing the cryoablation is provided with a particularly accurate control of an upcoming diaphragmatic palsy.

It is also provided a computer program comprising instructions for performing the monitoring method, a computer-readable data storage medium having recorded thereon the computer program, and a control unit comprising a processor coupled to a memory, the memory having recorded thereon the computer program. The control unit thereby forms a computer system configured to monitor diaphragmatic response to phrenic nerve stimulation by executing the monitoring method. The control unit thereby constitutes a device that monitors, in real-time (e.g. and automatically) by executing the monitoring method, diaphragmatic response to phrenic nerve stimulation. The control unit thus forms a tool that assists a surgeon during cryoablation by providing him/her with a control of upcoming diaphragmatic palsy.

The control unit may be included in a system that also includes any one or any combination of a first plurality of electrodes configured to measure the CMAP signal, a second plurality of electrodes configured to measure the ECG signal, a phrenic nerve stimulation system, and/or a cryoablation catheter (e.g. a cryoballoon catheter). The phrenic nerve stimulation system may comprise a phrenic nerve stimulation catheter. The phrenic nerve stimulation catheter may for example be as illustrated on FIG. 1. Alternatively, the phrenic nerve stimulation catheter may be configured to perform phrenic nerve stimulation in cooperation with other means of the phrenic nerve stimulation system, such as a patch. The phrenic nerve stimulation system may for example be as disclosed in European Patent Application EP21305287.1, which is incorporated herein by reference. The first plurality of electrodes may comprise one or more surface electrodes and/or one or more intravascular electrodes (e.g. electrodes inside a hepatic vein). The system may further comprise a display for outputting a visual alert when the threshold is passed, and/or a sound emitting device for outputting a sound alert when the threshold is passed. The display and/or the sound emitting device may be part of an electrophysiology monitoring and recording device that is connected to the system.

The control unit may be provided as an apparatus that includes a housing that houses the control unit. The apparatus also comprises the first plurality of electrodes, the second plurality of electrodes, the phrenic nerve stimulation catheter, and/or the cryoablation catheter. The first plurality of electrodes and/or the second plurality of electrodes may be provided detached from the housing and may be configured to be connected to the control unit via one or more electrical interfaces, e.g. provided on the housing. Alternatively, the first plurality of electrodes and/or the second plurality of electrodes may be provided already connected to the control unit via one or more electrical interfaces, e.g. provided on the housing, detachably or non-detachably. The housing may be configured to be connected to an electrophysiology monitoring and recording device that includes the previously-discussed display and/or sound emitting device, so that the control unit inside the housing transmits the CMAP signal to the recording device. For example, the housing may comprise one or more additional electrical interfaces configured to connect the housing to the electrophysiology monitoring and recording device.

The monitoring method may be used during phrenic nerve stimulation, for example during a cryoablation. In that respect, it is also proposed a method of phrenic nerve stimulation and a method of cryoablation, which may be respectively referred to as "the stimulation method" and "the cryoablation method".

The stimulation method comprises performing phrenic nerve stimulation (by any known phrenic nerve stimulation method, for example the method discussed in reference to FIG. 1 or the method of phrenic nerve stimulation disclosed in previously-cited European Patent Application EP21305287.1), and, while performing the phrenic nerve stimulation, monitoring a diaphragmatic response to the phrenic nerve stimulation by executing the monitoring method.

The cryoablation method comprises: introducing a cryoablation catheter inside a left atrium of a human patient, performing cryoablation, while performing cryoablation, repeating the stimulation method, and, when an alert is outputted as the threshold is passed, pausing the cryoablation and then resuming the cryoablation (e.g. when diaphragmatic response comes back to normal, e.g. to 90% or 100% of its normal amplitude, and/or when the alert ends).

The monitoring method is now further discussed.

The monitoring method is for monitoring diaphragmatic response to phrenic nerve stimulation. In other words, the monitoring method is executed during execution of a phrenic nerve stimulation process, and monitors a diaphragmatic response to the stimulation. The phrenic nerve stimulation process may comprise several phrenic nerve stimulation occurrences (i.e. performed while the monitoring method is executed), e.g. at a predetermined frequency, for example between 40 and 100 stimulations per minute, e.g. 60 stimulations per minute or of such order of magnitude.

The monitoring method is computer-implemented and the method steps are executed by a control unit, which is a computer system executing the monitoring method. This means that steps (or substantially all the steps) of the monitoring method are executed by the control unit. Thus, steps of the monitoring method are performed by the control unit, possibly fully automatically (for example, all the method steps may be executed automatically by the control unit), or, semi-automatically. In particular, the step of repeating in real-time the detecting, monitoring, computing, comparing and outputting may be performed automatically (in other words, the real-time detecting, monitoring, computing, comparing and outputting are automatically performed repeatedly). In examples, the triggering of at least some of the steps of the monitoring method may be performed through user-interaction with the control unit or with a housing that houses the control unit. The level of user-interaction with the control unit required may depend on the level of automatism foreseen and put in balance with the need to implement user's wishes. In examples, this level may be user-defined and/or pre-defined.

The control unit may comprise a processor coupled to a memory, the memory having recorded thereon a computer program comprising instructions for performing the monitoring method. The memory may also store a database. The memory is any hardware adapted for such storage, possibly comprising several physical distinct parts (e.g. one for the program, and possibly one for the database). The processor may also be coupled to a display (e.g. a Graphical User Interface (GUI)) for outputting a visual alert when the threshold is passed. The processor may additionally or alternatively be coupled to a sound emitting device (e.g. a speaker) for outputting a sound alert when the threshold is passed.

Figure 2:
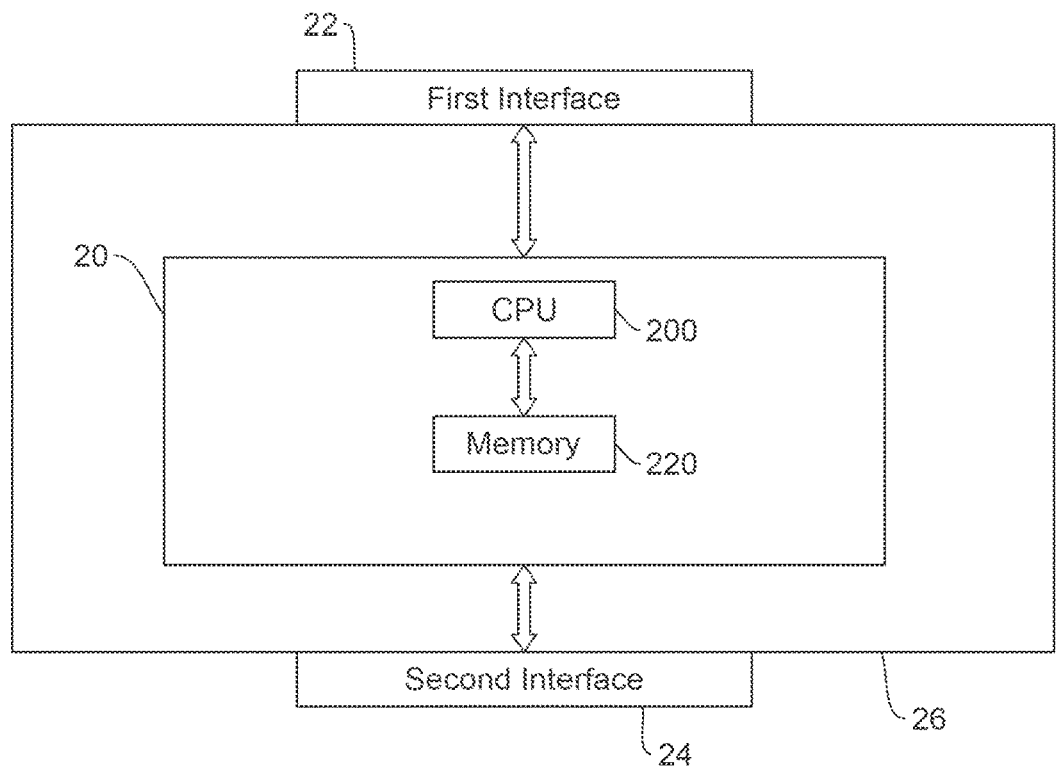
FIGS. 2 to 11 illustrate the methods, the control unit, and the system.

FIG. 2 shows a schematic representation of an example of the control unit. More specifically, FIG. 2 shows a schematic representation of a housing 26 that houses the control unit 20. Control unit 20 comprises a CPU (central processing unit) 200 coupled to memory 220, memory 220 having recorded thereon a computer program comprising instructions for performing the monitoring method. As shown on FIG. 2, electrical interfaces 22 and 24 are provided on housing 26. Electrical interfaces 22 and 24 are connected to control unit 20. First electrical interface 22 is configured to be connected to one or more electrodes configured to measure/acquire the CMAP signal. Second electrical interface 24 is configured to be connected to one or more electrodes configured to measure/acquire the ECG signal. Although not shown on FIG. 2, housing 26 may comprise one or more other electrical interfaces configured to be connected to a display for outputting a visual alert when the threshold is passed and/or to a sound emitting device for outputting a sound alert when the threshold is passed. Said other electrical interface(s) may for example be configured to be connected to an electrophysiology monitoring and recording device that includes the display and/or the sound emitting device. Alternatively, the housing 26 may directly comprise such a display and/or sound emitting device.

The computer program may comprise instructions executable by a computer such as the control unit, the instructions comprising means for causing the above system to perform the monitoring method. The program may be recordable on any data storage medium, including the memory of the system. The program may for example be implemented in digital electronic circuitry, or in computer hardware, firmware, software, or in combinations of them. The program may be implemented as an apparatus, for example a product tangibly embodied in a machine-readable storage device for execution by a programmable processor. Method steps may be performed by a programmable processor executing a program of instructions to perform functions of the monitoring method by operating on input data and generating output. The processor may thus be programmable and coupled to receive data and instructions from, and to transmit data and instructions to, a data storage system, at least one input device, and at least one output device. The application program may be implemented in a high-level procedural or object-oriented programming language, or in assembly or machine language if desired. In any case, the language may be a compiled or interpreted language. The program may be a full installation program or an update program. Application of the program on the system results in any case in instructions for performing the monitoring method.

The monitoring method comprises receiving in real-time a CMAP signal of a human patient. The diaphragmatic CMAP signal may be received from, and measured by, a first plurality of electrodes, which may include one or more surface electrodes and/or one or more intravascular electrodes (e.g. electrodes inside a hepatic vein). The one or more surface electrodes allow to measure the CMAP signal with simplicity. The one or more intravascular electrodes form a solution to measure the CMAP signal with improved accuracy. The monitoring method may thus comprise, by the first plurality of electrodes, measuring in real-time the diaphragmatic CMAP signal of the human patient, and transmitting in real-time the measured diaphragmatic CMAP signal to the control unit, which receives it in real-time. The CMAP signal is a signal capturing a muscular motor response of the diaphragm to a phrenic nerve stimulation. The concept of CMAP is well known. The receiving in real-time of the CMAP signal may occur continuously during execution of the method.

Measurement of the CMAP signal and examples of this measurement are now discussed.

The CMAP signal may be measured by one or more surface electrodes as previously discussed, for example by two surface electrodes. This may consist in positioning the two electrodes (e.g. standard ECG electrodes) on the costal edge, the measurement of the signal being carried out in a bipolar mode between the two electrodes. This measurement method is simple in its set-up and non-invasive. When the CMAP signal is measured in this manner, it may become difficult to visually interpret in real-time as the signal tends to have a rounded shape that makes difficult the evaluation of its amplitude modifications in real-time. But the monitoring method overcomes this difficulty by computing objectively the real-time value of the characteristic of the CMAP. Furthermore, the surface electrodes measure not only the CMAP signal but also the ECG, which may have an amplitude that is in average equal to that of the CMAP, making the analysis of the CMAP possibly difficult when there is synchronicity between the CMAP and a QRS complex in the ECG). But the method overcomes this difficulty as well, as the real-time value of the characteristic of the CMAP is asynchronous to the QRS complex in the ECG.

Figure 3:
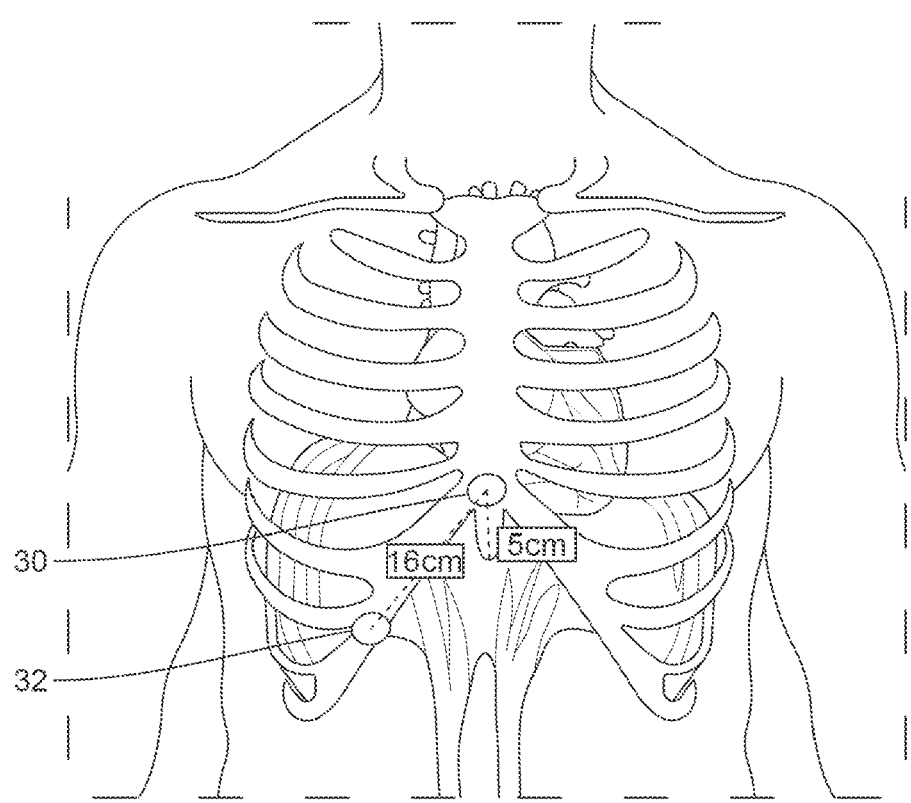

FIG. 3 shows an example of the CMAP signal measurement. In this example, the measurement is performed using two surface electrodes 30 and 32. FIG. 3 illustrates an example of the positioning of these cutaneous electrodes.

Figure 4:
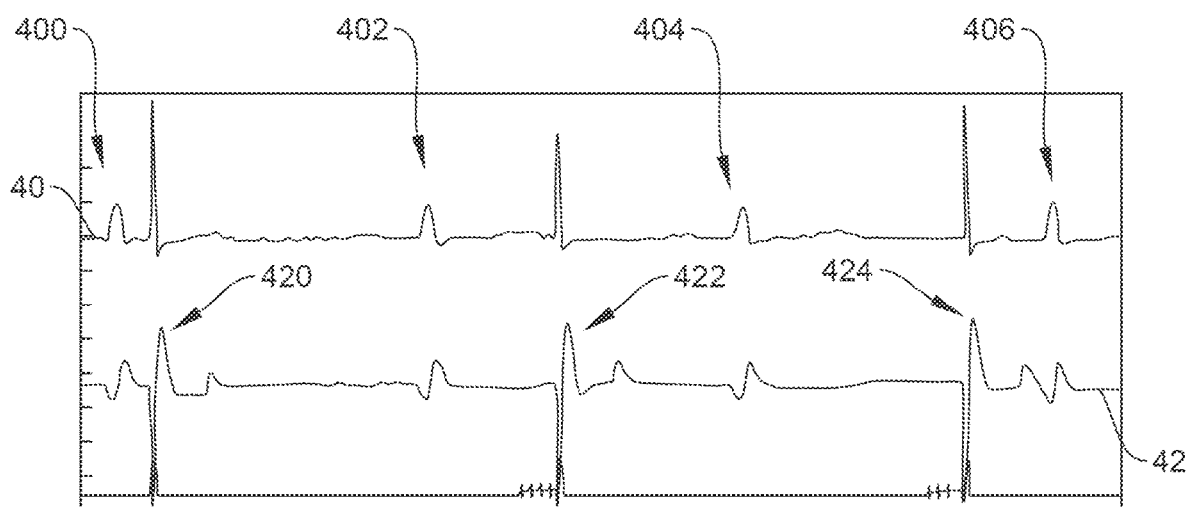

FIG. 4 shows a CMAP signal measured according to this example. The top curve 40 corresponds to a measured ECG in bipolar derivation between right and left hand wrist (possibly referred to as a "DI derivation", or "Derivation I"). Other derivations may be used to measure the ECG, that of FIG. 4 being only an example. Up to twelve derivations (six bipolar and six unipolar) may be used for measuring the ECG as known per se, providing as many different viewpoints of the cardiac electrical activity. The DI derivation corresponds to all the vectors that go from right to left, as known per se. The bottom curve 42 corresponds to the measured CMAP. Time events 400, 402, 404 and 406 correspond to cardiac electrical activity, in particular QRS complexes (corresponding to the depolarization of ventricles). Time events 420, 422 and 424 corresponds to CMAP potentials (including peaks), each preceded by a stimulation artefact. As can be seen from FIG. 4, the occurrences 400, 402, 404 and 406 of the QRS complex disturb the CMAP signal 42, making the signal temporarily leave its isoelectric line (i.e. horizontal line above and below which the curve representing the CMAP signal is centered).

Alternatively, the CMAP signal may be measured by a quadrupolar electrophysiology catheter positioned in a hepatic vein (e.g. the most posterior possible, which is the closest possible to the diaphragm, as this works best for the measurement). The vein may be selected by a practician. The positioning of the catheter is simple, non-traumatic and painless. It provides a CMAP that is easily interpretable, having a pointy aspect that makes it easily measurable. This measurement method reduces visual impact of the ECG. However, when there is a synchronicity between the QRS and the CMAP, the CMAP amplitude may be modified. As previously explained, the monitoring method overcomes this difficulty by having the computed real-time value of the characteristic asynchronous to the ECG QRS complex.

Figure 5:
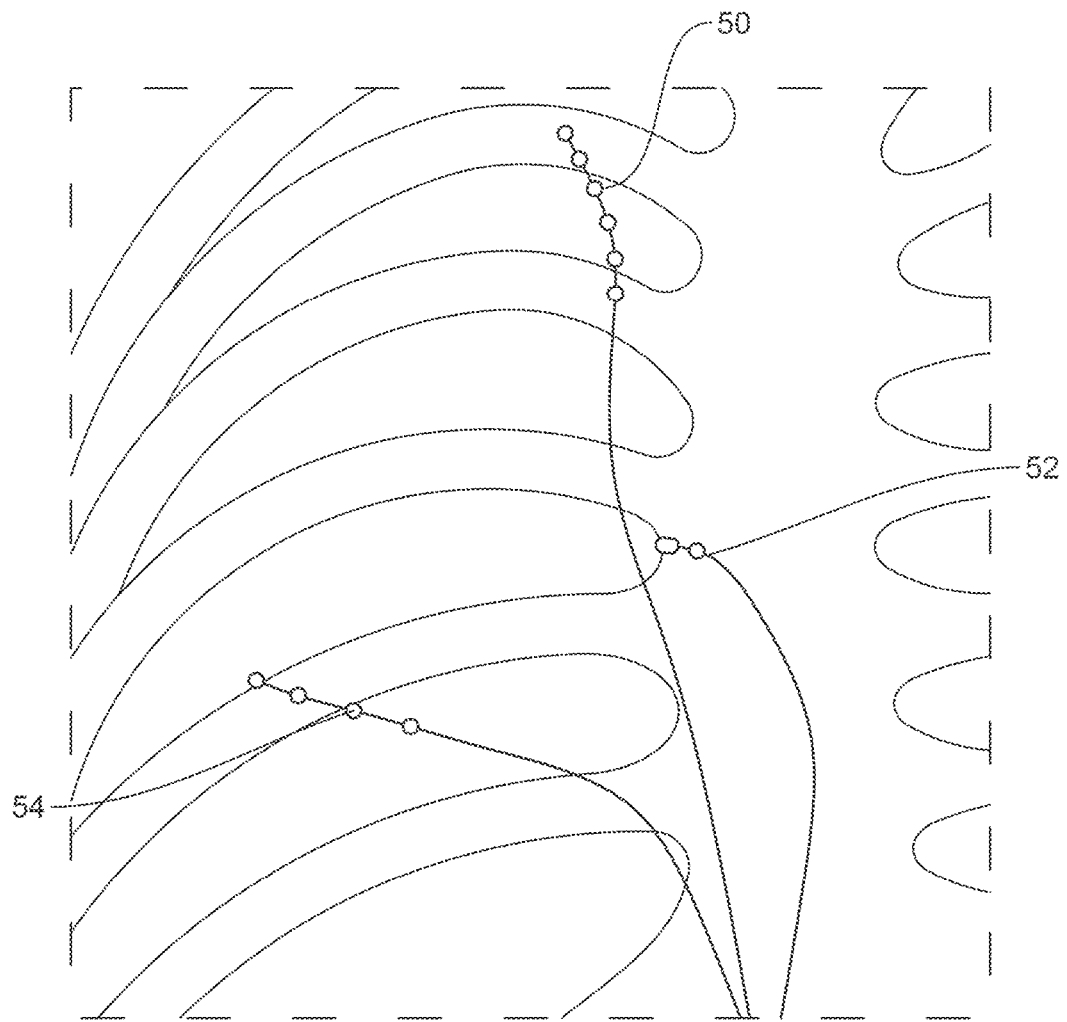
Figure 6:
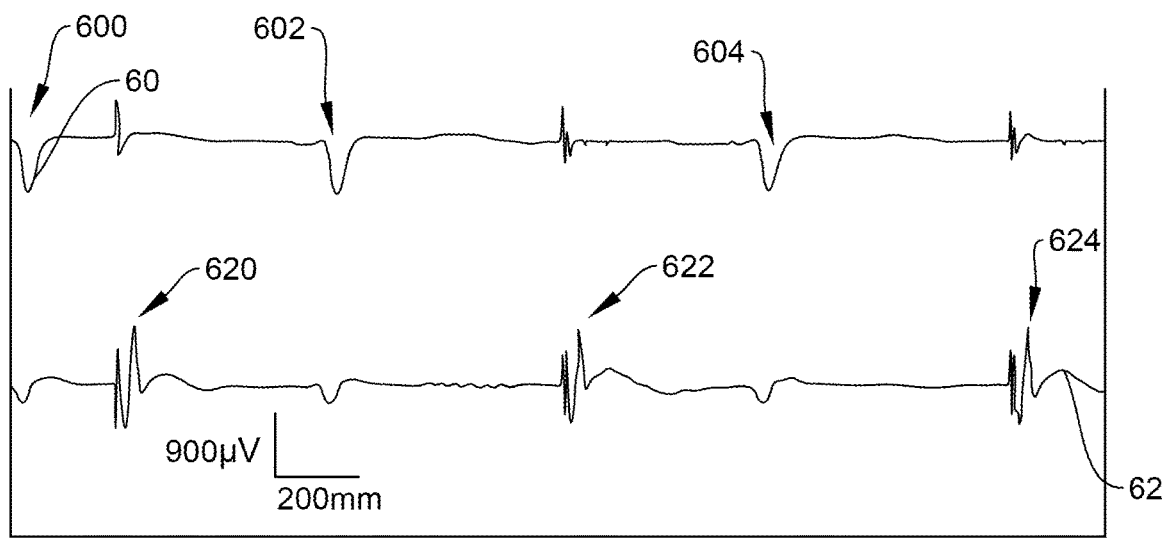

FIG. 5 shows an example of such a measurement method during cryoablation. As shown on FIG. 5, top catheter 50 (comprising six electrodes) is positioned in the superior vena cava to stimulate the right phrenic nerve. Middle catheter 52 is a cryoballoon positioned in a right pulmonary vein. Bottom catheter 54 (comprising four electrodes) is positioned in a hepatic vein. FIG. 6 shows an example of the CMAP signal measured by such a method. Top curve 60 shows the ECG signal. Bottom curve 62 shows the CMAP signal measured by catheter 54. Time events 600, 602, and 604 correspond to QRS complexes. Time events 620, 622 and 624 corresponds to CMAP potentials (including peaks), each preceded by a stimulation artefact. As can be seen from FIG. 6, the occurrences 600, 602, 604 of the QRS complex disturb the CMAP signal 42, making the signal temporarily leave its isoelectric line.

Figure 7:
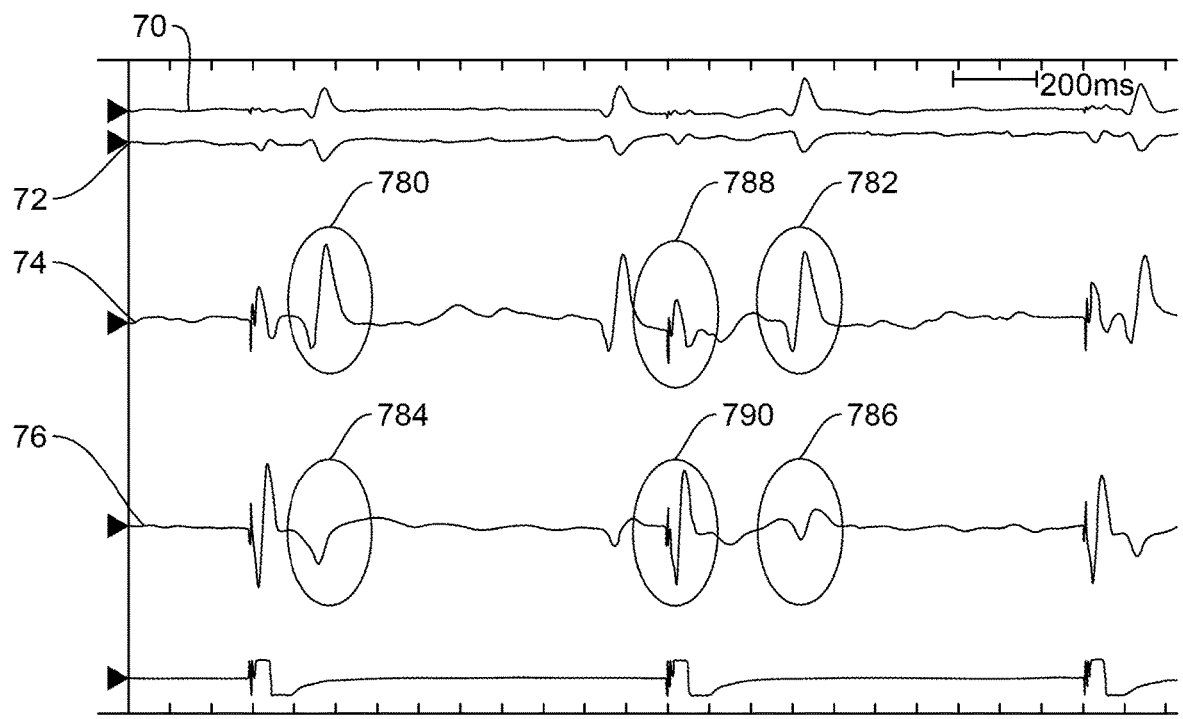

FIG. 7 shows an example of a simultaneous measurement of the CMAP signal by both a catheter in a hepatic vein and surface electrodes. Top curves 70 and 72 correspond to the ECG signal. Curve 74 corresponds to the CMAP signal measured by the surface electrodes. Curve 76 corresponds to the CMAP signal measured by the hepatic catheter. Circles 780, 782, 784 and 786 show portions of the CMAP signal synchronous to measured QRS complexes, thereby illustrating how synchronicity of the QRS complex with the CMAP signal affects the CMAP signal, making the signal temporarily leave its isoelectric line. Circles 788 and 790 show CMAP potentials (including peaks). As shown in FIG. 7, the amplitude ratio of the CMAP over the ECG is larger for the hepatic measurement, making its interpretation easier.

Figure 8:
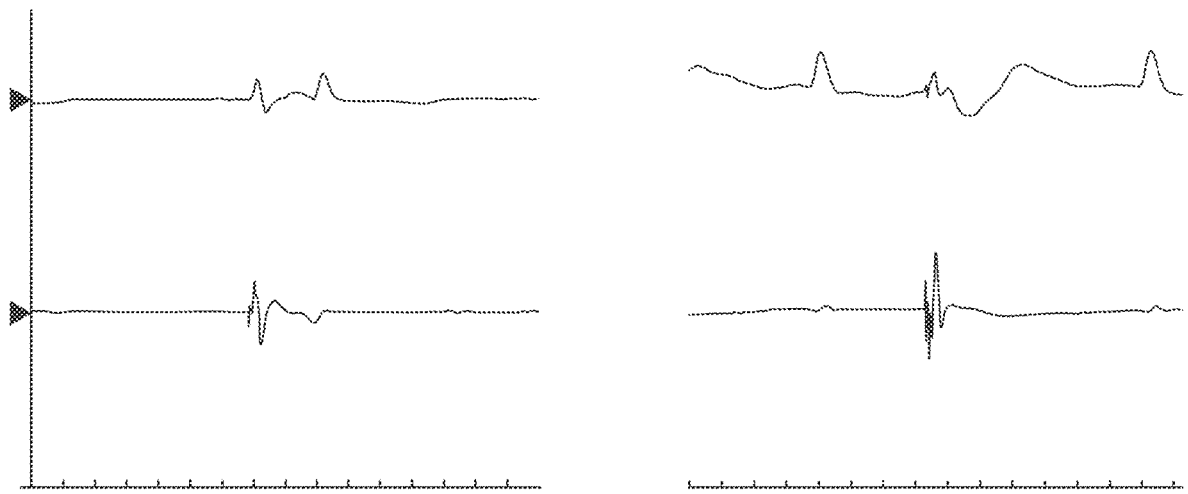

FIG. 8 illustrates other examples of simultaneous measurement by surface electrodes (top curves) and a hepatic catheter (bottom curve).

Figure 9:
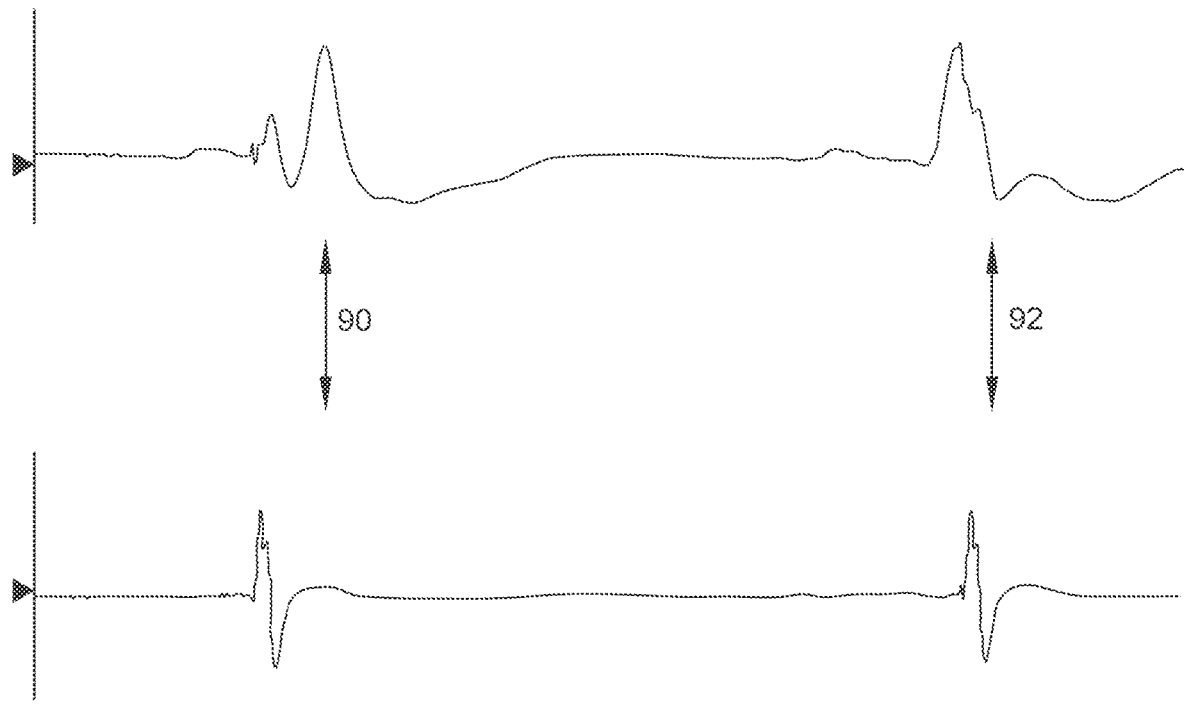

FIG. 9 illustrates an example of simultaneous occurrence of a QRS and of a CMAP potential, thereby illustrating synchronicity between the QRS and the CMAP. The top curve corresponds to a measurement by surface electrodes, and the bottom curve corresponds to a measurement by a hepatic catheter. On the top curve, the first time event 90 is a stimulation artefact followed by a CMAP potential that is simultaneous to a QRS. The second time event 92 is a QRS that includes a CMAP potential in its last portion. For both events, the amplitude of the CMAP measured by surface electrodes is difficult or even impossible to determine as is. The hepatic CMAP remains interpretable in this example, however in practice it is often not the case when it is simultaneous to the QRS. As previously explained, the method overcomes these difficulties.

The monitoring method comprises, computing a baseline value of a characteristic of the CMAP signal. The baseline value is a reference value of the characteristic of the CMAP signal, e.g. a value of the characteristic of the human patient in standard conditions (e.g. when the patient is at rest, for example before starting a cryoablation).

The characteristic of the CMAP signal is any attribute or feature of the CMAP signal that represents a diaphragmatic response intensity to a phrenic nerve stimulation. The characteristic may for example be an attribute of the CMAP signal that captures the variations of the CMAP signal in a manner allowing diaphragmatic response intensity analysis based on the characteristic. The characteristic is a function of any portion of the CMAP signal that substantially corresponds to a diaphragmatic response to phrenic nerve stimulation, e.g. the time interval corresponding to the portion of the CMAP signal is substantially the time interval of the response or of a significant and/or relevant part of the response (e.g. a potential of the response). This excludes portions of the CMAP signal that do not correspond to a diaphragmatic response, such as a portion corresponding to a time interval that only overlaps, but do not correspond to, the time interval of a response or of a significant part thereof. The method repeatedly computes a real-time value of the characteristic, i.e. the method repeatedly and in real time computes the value of the characteristic on several portions of the CMAP signal each corresponding to a diaphragmatic response. This computation may include computing the real-time value for each occurrence of a diaphragmatic response, by using for each occurrence the CMAP signal portion corresponding to the response. This computation may additionally or alternatively include computing an average value of the characteristic for several occurrences of the response, by using the CMAP signal portions corresponding to these occurrences. As further discussed hereinafter, a portion of the CMAP signal that substantially corresponds to a diaphragmatic response may in some cases also be synchronous to a QRS complex occurrence. In such a case, the value of the characteristic is not computed on this portion, the diaphragmatic response corresponding to this portion being thereby discarded.

The characteristic may for example be an amplitude between two consecutive peaks of the CMAP signal. The two consecutive peaks may be a bottom peak of a CMAP potential and a top peak of the CMAP potential, e.g. upon an event such as the triggering of a stimulation, the CMAP signal leaves its isoelectric line, then reaches the bottom peak and then the top peak (or the other way around, depending e.g. on polarity of the electrodes), and then returns to the isoelectric line (as notably shown on FIG. 11, discussed hereinafter). The two consecutive peaks define a portion of the CMAP signal, i.e. the CMAP potential, corresponding to a time interval between the two peaks, on which the real-time value of the characteristic may be computed (e.g. by computing a CMAP measure substantially on this portion). In other words, the characteristic may be a function of this portion, that substantially corresponds to a diaphragmatic response. On this portion, the CMAP signal forms a CMAP potential. Alternatively, the characteristic may be an area between a curve portion representing two consecutive peaks of the CMAP signal and the isoelectric line. In such a case, the monitoring method may process a curve representing the CMAP signal, and may compute an area below this curve and the isoelectric line (where the area is always computed as a positive value, be the curve above or below the isoelectric line, e.g. an integral of a distance from the curve to the isoelectric line). Here, the time interval may start at the beginning of the first peak and end at the end of the second peak. For example, the area may be computed as a sum between a first area between the isoelectric line and a first sub-portion of the curve forming a first peak (i.e. said first sub-portion starting where the curve leaves the isoelectric line and ending where the curve rejoins the isoelectric line), and a second area between the isoelectric line and a second sub-portion forming a second peak consecutive to the first peak (i.e. said second sub-portion starting where the first sub-portion ends—the curve in fact crossing the isoelectric line there—and ending where the curve rejoins the isoelectric line), the first and second peaks being consecutive and forming a CMAP potential.

The computing of the baseline value may be carried out at the beginning of the method, i.e. as an initial step, for example when the patient is at rest (e.g. before a cryoablation starts). For example, the computing of the baseline value may be carried out shortly after an activation of the control unit (which is discussed hereinafter), and may for example be automatically triggered by pressing a button (e.g. a "REF" button) of a housing that houses the control unit. The baseline value may correspond to a value of the signal larger than 0.3 mV for the monitoring to be performed in good conditions. The monitoring method may start the monitoring of the CMAP signal only when the baseline value is larger than 0.3 mV and when there is no instability, to ensure good conditions for the monitoring. By «instability», it is meant unwanted variations of the CMAP signal or of the characteristic of the CMAP signal, such as variations of the characteristic from one stimulation to the next that are higher than 10%, for example higher than 30%. Such instability may be due to instability of the measuring of the CMAP and/or instability of the phrenic nerve stimulation. These variations may be caused by the measurement method used for measuring the CMAP signal, which for example may have a quality that varies in time. Contrary to a potential upcoming diaphragmatic palsy, the instability may indicate increases and drops of the CMAP signal, i.e. random variations. Upcoming diaphragmatic palsy may rather be indicated by a continuous decrease of the CMAP signal, e.g. to arrive at a certain drop (e.g. of 30%) in a certain time (e.g. 10 s to 20 s), while an occurring diaphragmatic palsy corresponds to CMAP signal that has vanished. The monitoring method may, before monitoring the CMAP signal, output a (e.g. visual and/or sound) indication that the conditions to monitor the CMAP signal (stability and/or a baseline value larger than 0.3 mV) are met.

The method further comprises determining a threshold value of the characteristic. The determining of the threshold value may be carried out at the beginning of the method, i.e. as an initial step which also comprises the computing of the baseline value, for example when the patient is at rest (e.g. before a cryoablation starts). The determining of the threshold value is based on the computed baseline value, and includes shifting the baseline value. By "shifting", it is meant that the threshold equals the baseline value minus or plus a certain amount (e.g. a certain percentage of the baseline value). For example, the determining of the threshold value may comprise determining a predefined drop (e.g. in terms of percentage, e.g. between 25% and 35%, for example 30%) of the computed baseline value. The threshold value represents a boundary of values of the characteristic indicative of upcoming diaphragmatic palsy, i.e. the value of the characteristic passing this boundary indicates (i.e. is representative of) an upcoming diaphragmatic palsy. The boundary may be a lower boundary, i.e. the value of the characteristic being lower than this boundary indicates an upcoming palsy. For example, the threshold value may correspond to a maximal drop of the baseline value, and the value of the characteristic being lower than this maximal drop indicates an upcoming palsy. Alternatively, the boundary may be an upper boundary the value of the characteristic being higher than this boundary indicates an upcoming palsy. This may for example be the case when the characteristic is a function of the inverse of another characteristic for which the boundary is a lower boundary.

In examples, the threshold value corresponds to a drop of the baseline value which is larger than 25% and/or lower than 35%, for example equal to 30%. By "drop of x % of the baseline value", it is meant that the threshold value equals the baseline value minus x % of the baseline value, x % being the drop. For example, threshold=(1−x %)*baseline, x % being the drop and being a percentage. In examples, x % is comprised between 25% and 35%, for example x %=30%. A drop larger than 25% allows to avoid false positives (i.e. to avoid false detection of upcoming diaphragmatic palsy). A drop lower than 35% allows to detect upcoming diaphragmatic palsy in time (e.g. before it inevitably occurs). A drop of 30% (e.g. +/−1%) provides a best compromise between sensitivity and specificity. A drop of 30% (e.g. +/−1%) of the baseline value is not perceivable by abdominal palpation, and the time frame between the drop of 30% and the effective palsy is on average of about 30 s. Thereby, the threshold value of 30% (e.g. +/−1%) allows the detection in time of an upcoming diaphragmatic palsy that cannot be detected by hand (e.g. even by a medical professional). Stop of a cryoablation when an alert is outputted because the 30% threshold value has been passed allows to avoid or drastically reduces risks of palsy, in which case the CMAP then regains 100% of its value in less than a minute.

The monitoring method further comprises receiving in real-time an ECG signal of the human patient. The ECG signal may be received from, and measured by, a second plurality of electrodes. The monitoring method may thus comprise, by the second plurality of electrodes, measuring in real-time the ECG signal of the human patient, and transmitting in real-time the measured ECG signal to the control unit, which receives it in real-time. The receiving in real-time of the ECG signal may occur continuously during execution of the method.

The monitoring method further comprises, repeating in real-time (e.g. repeatedly and continuously, and while receiving the CMAP signal and the ECG signal):
- detecting a QRS complex in the ECG signal (i.e. detecting occurrences of the QRS in the signal);
- monitoring the CMAP signal;
- computing a real-time value of the characteristic, the real-time value of the characteristic being asynchronous to the QRS complex;
- comparing the real-time value to the threshold value; and
- outputting an alert when the threshold is passed.

Figure 10:
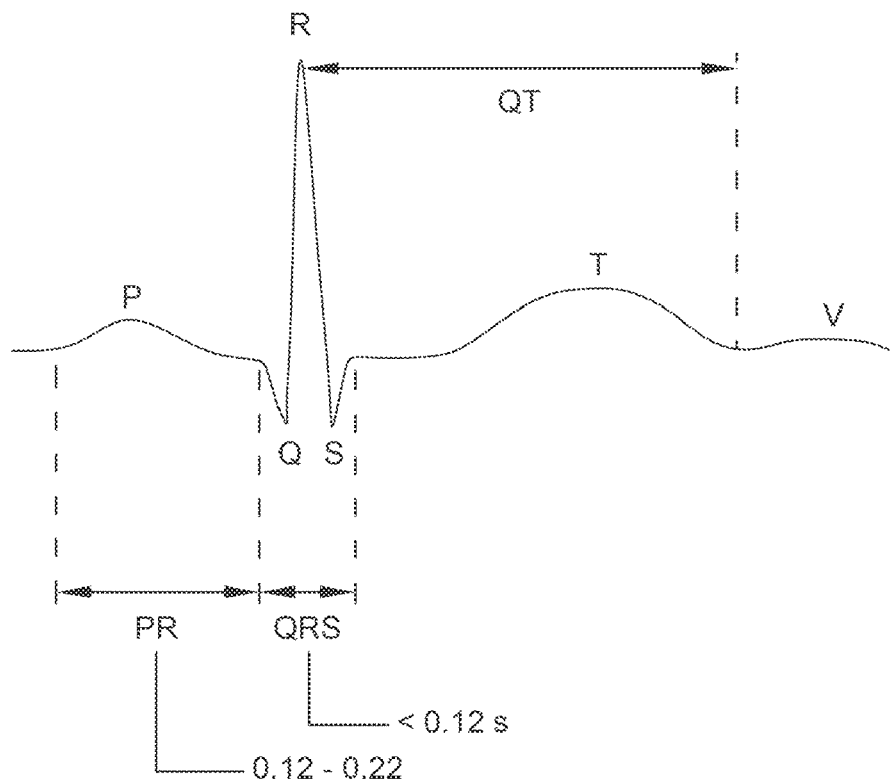

The detection of the QRS complex in the ECG signal may be carried out by any known method designed for such detection. Detecting a QRS complex in the ECG is widely known in the art. FIG. 10 illustrates the concept of QRS complex. As shown on FIG. 10, the ECG is composed of several waves: wave P that corresponds to the depolarization of the cardiac atrium, wave QRS that corresponds to the depolarization of the ventricles, and T wave that corresponds to the repolarization of the ventricles. In an ECG, the QRS has the larger amplitude and thus affects the most the CMAP monitoring. As known per se, each occurrence of the QRS corresponds to a portion of the ECG signal that has a given time length (which may depend on the patient and vary over different patients), with a given beginning time and a given end time. The beginning time is the time at which the ECG signal leaves its isoelectric line, the ending time being the time at which the ECG signal then returns to its isoelectric line. The time length of the QRS may be comprised between 60 ms and 200 ms, generally (i.e. for standard patients in general) between 60 ms and 100 ms.

The monitoring of the CMAP signal may be carried out by any known method designed for such monitoring.

The computing of the real-time value of the characteristic is performed so as to make the real-time value of the characteristic asynchronous to the QRS complex. In other words, the method evaluates repeatedly and continuously the real-time value of the characteristic, and the method is such that each evaluation is based only on a respective (possibly discontinuous) portion of the CMAP signal during which no QRS complex occurs (i.e. no substantially no QRS complex occurs during the time interval or time intervals defining said respective portion).

By "asynchronous", it is thus meant that the real-time value of the characteristic is computed on portions of the CMAP signal each corresponding to a diaphragmatic response as previously discussed but each not corresponding to (i.e. separate/distinct from) any occurrence of the QRS complex. Such a portion, of which the characteristic is a function as previously discussed, is a portion of the CMAP signal that is asynchronous to the QRS complex. A portion of the CMAP signal that is asynchronous to the QRS complex is thus a portion of the CMAP signal that corresponds to a time interval that does not overlap any time interval corresponding to a QRS occurrence. Conversely, a portion of the CMAP signal is synchronous to the QRS complex if the portion corresponds to a time interval that overlaps a time interval corresponding to a QRS occurrence (i.e. the time interval beginning at the beginning time of the QRS occurrence and ending at the end time of the QRS occurrence). Thus, a portion of the CMAP signal asynchronous to the QRS complex corresponds to a time interval substantially outside any time interval corresponding to a QRS occurrence. Thus, "the real-time value of the characteristic being asynchronous to the QRS complex" is synonymous to the "the real-time value of the characteristic being computed on CMAP signal portions each corresponding to a time interval that corresponds to a diaphragmatic response but that does not overlap any time interval corresponding to a QRS occurrence".

The monitoring method may comprise discarding diaphragmatic responses synchronous to detected QRS complexes. In other words, in this case, the CMAP signal portions that correspond to diaphragmatic responses synchronous to QRS complexes are not used for computing the real-time value of the characteristic (i.e. the computation is not done for these portions), i.e. these responses are not taken into account by the method for the computation of the real-time value of the characteristic. In yet other words, the method may (e.g. upon detection of the QRS complex occurrences) identify any portion of the CMAP signal that is synchronous to the QRS complex and avoid computing the real-time value of the characteristic based on this portion. This allows to avoid interferences of the QRS in the computation of the real-time value of the characteristic.

Additionally or alternatively, the monitoring method may further comprise commanding phrenic nerve stimulation. The monitoring method comprises in such a case triggering an occurrence of the phrenic nerve stimulation a predetermined amount of time after detection of an occurrence of the QRS complex such that a diaphragmatic response to the triggered occurrence of the phrenic nerve stimulation occurs and ends before a next occurrence of the QRS complex. The predetermined amount of time after detection of the QRS occurrence may be a predetermined amount of time after the ending point of the QRS occurrence. Alternatively, the predetermined amount of time after detection of the QRS occurrence may be a predetermined amount of time after the beginning point of the QRS occurrence. The predetermined amount of time may be lower than 500 ms, for example comprised between 10 ms and 500 ms, for example equal to 200 ms. Thereby, all or at least a significant part of the diaphragmatic responses to phrenic nerve stimulations may correspond to portions of the CMAP signal asynchronous to any QRS complex occurrence. This allows to ensure, as the diaphragmatic response is in this manner asynchronous to the QRS complex, that the real-time value of the characteristic is asynchronous to the QRS complex.

The triggering of the occurrence of the phrenic nerve stimulation a predetermined amount of time after detection of an occurrence of the QRS complex may be carried out instead of the discarding of diaphragmatic responses synchronous to detected QRS complexes, as an alternative manner to ensure that the real-time value of the characteristic is asynchronous to the QRS complex. Alternatively, the triggering of the occurrence of the phrenic nerve stimulation a predetermined amount of time after detection of an occurrence of the QRS complex and the discarding of diaphragmatic responses synchronous to detected QRS complexes may be both carried out. This further increases safety of the monitoring, i.e. further ensures that the real-time value of the characteristic is asynchronous to the QRS complex.

The real-time value of the characteristic may be an average of the characteristic for several occurrences of the phrenic nerve stimulation, for example a sliding average. In other words, the method may compute, e.g. continuously and in real-time during the monitoring, several values of the characteristic each for a respective occurrence of the phrenic nerve stimulation, and compute, also continuously and in real-time, the real-time value as an average of these several values. In yet other words, in this case the real-time value is a real-time (e.g. sliding) average of real-time values of the characteristic each for a phrenic nerve stimulation occurrence. The real-time value of the characteristic may be an average of the characteristic for a predetermined number of consecutive occurrences of the phrenic nerve stimulation, the predetermined number being for example below or equal to 5, for example equal to 2, 3, 4 or 5.

Using the average of the characteristic increases robustness to synchronicity to the QRS complex and also allows to efficiently compute the real-time value despite possible instabilities of the phrenic nerve stimulation. In other words, the averaging makes the monitoring robust to a possible instability of the stimulation. A low predetermined number of occurrences (e.g. 2 or 3) may be sufficient in the case of a stable phrenic nerve stimulation such as the one achieved by the system and method for phrenic nerve stimulation disclosed in European Patent Application EP21305287.1. In such a case, the diaphragmatic response is very reliable and need not being averaged over a large window. This allows higher "real-time-ness", i.e., higher responsiveness. By "stable", it is meant that slight movements of intravascular electrodes that perform the stimulation do not affect the stimulation.

The computing of the real-time value of the characteristic may comprise calculating one or more CMAP measures performed each on a portion of the CMAP signal beginning at a predetermined amount of time after an occurrence of the phrenic nerve stimulation and lasting for a predetermined time duration after the occurrence of the phrenic nerve stimulation. The portion may substantially correspond to a time interval between two consecutive peaks of a CMAP potential yielded by the stimulation or covering exactly two consecutive peaks of such a CMAP potential, as previously discussed. Each measure may be a measure of an amplitude difference between two consecutives peaks (e.g. upper and top peaks, as previously discussed) of the CMAP signal, or a measure of an area between the isoelectric line and a curve representing the CMAP signal. The method may use each measure to compute the real-time value of the characteristic, for example by performing an average of the measures as previously discussed. The predetermined amount of time after an occurrence of the phrenic nerve stimulation corresponds to a time window of the stimulation, and the predetermined time duration after the occurrence of the phrenic nerve stimulation corresponds to a time window of analysis of the CMAP that follows the time window of the stimulation. Thereby each measure of the CMAP used in the computing of the real-time value corresponds to a time window of the CMAP signal that is not perturbated by the stimulation artefact in the CMAP signal. The predetermined amount of time may be larger than 3 ms and/or lower than 50 ms, for example comprised between 10 ms and 20 ms. Additionally or alternatively, the predetermined time duration may be larger than 50 ms and/or lower than 150 ms, for example comprised between 50 ms and 100 ms, e.g. equal to 100 ms.

Figure 11:
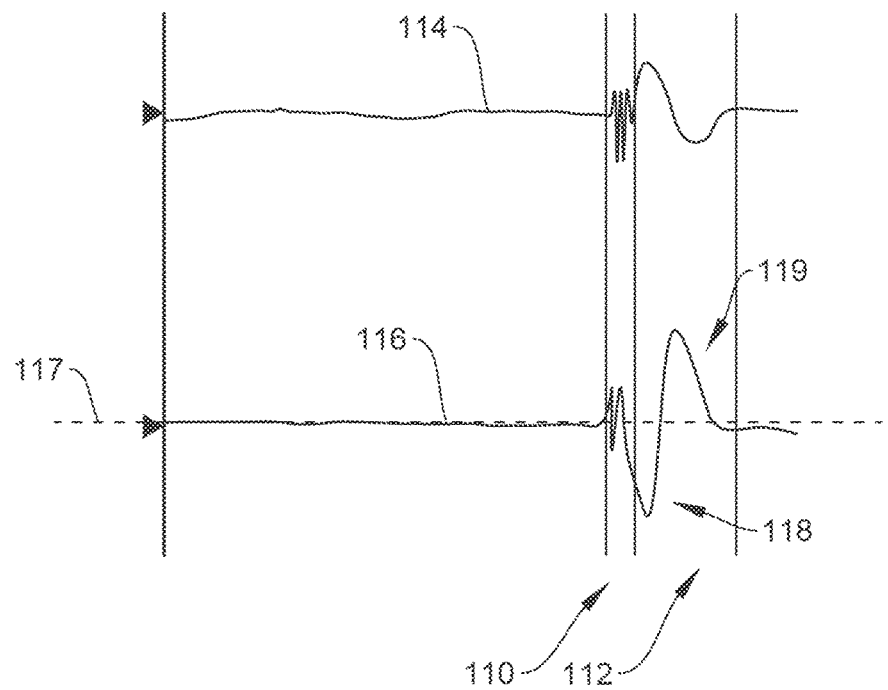

FIG. 11 illustrates the predetermined amount of time and the predetermined time duration on curves 114-116 representing the CMAP signal. On FIG. 11, curve 114 is a curve representing a CMAP signal measured by surface electrodes, curve 116 is a curve representing a CMAP signal measured by a hepatic catheter. Time interval 110 corresponds to a stimulation artefact. Time interval 112 corresponds to the time of measurement of the CMAP: it starts after the predetermined amount of time 110, substantially at a first (e.g. bottom) peak of a CMAP potential yielded by the stimulation, and lasts for the duration 112. The CMAP measure may be an amplitude between two consecutive peaks 118 and 119 of the CMAP signal, e.g. the bottom peak 118 and the top peak 119 of the CMAP potential shown on FIG. 11, or the area of first peak 118 (i.e. between curve 116 and isoelectric line 117 for the time interval corresponding to peak 118) plus the area of second peak 119 (i.e. between curve 116 and isoelectric line 117 for the time interval corresponding to peak 119), both areas being computed as positive values.

The comparing of the real-time value to the threshold value may be any comparison between the real-time value and the threshold value, for example an assessment of a difference and/or a ratio between the real-time value and the threshold value. The comparing may for example comprise assessing whether or not a ratio between the real-time value and the threshold value is (e.g. strictly) lower than 1 and/or whether or not a difference between the real-time value and the threshold value is (e.g. strictly) negative.

Then, when the threshold is passed, the monitoring method outputs an alert, i.e. an alert is outputted when the comparison results in that the real-time value is lower than the threshold value. The alert may be any indication that the threshold is passed, such as a sound alert, the outputting comprising then transmitting to a sound emitting device connected to the control unit an instruction to output an alert and emitting, by the sound emitting device, a sound alert. Additionally or alternatively (i.e. in addition to or instead of the sound alert), the alert may be a visual alert, the outputting comprising then transmitting to a display connected to the control unit an instruction to output an alert and displaying, by the display, a visual alert.

The monitoring method may comprise, as an initial step of the method, turning on or activating the control unit, for example by pressing a button (e.g. a "ON" button) of a housing that houses the control unit. Upon activation, the control unit then starts receiving (e.g. continuously, until deactivation of the control unit) the CMAP signal and the ECG signal, which are discussed hereinafter. Throughout the monitoring method, the monitoring method may comprise performing stimulations of the right phrenic nerve, e.g. at regular time steps, e.g. at a frequency comprised between 40 and 100 stimulations per minute, for example equal to 60 stimulations per minute.

The monitoring method may comprise, e.g. before performing the automatic and real-time repeating, ensuring that the CMAP signal is in proper conditions to be monitored. This improves robustness and accuracy of the monitoring method. The monitoring method may output an indication, e.g. in the form a visual and/or sound indication that the CMAP signal is not yet in proper conditions to be monitored. The ensuring may comprise filtering the CMAP signal as measured by the first plurality of electrodes (e.g. upon reception of the measured signal), for example at a frequency between 5 Hz and 150 Hz. The ensuring may additionally or alternatively comprise discarding portions of the CMAP signal that correspond to a signal 10% larger than the baseline value and/or portions corresponding to sharp variations of the CMAP signal (e.g. a drop larger than 20%). This may be indicative of an instability of the phrenic nerve stimulation. Alternatively or additionally to the discarding of the portions, the monitoring method may comprise outputting an indication of the instability of the phrenic nerve stimulation, e.g. in the form of a visual and/or sound indication.

The repeating in real-time of the detecting of the QRS complex in the ECG signal, of the monitoring of the CMAP signal, of the computing of the real-time value of the characteristic which is asynchronous to the QRS complex, of the comparing of the real-time value to the threshold value, and of the outputting of the alert when the threshold is passed, may be performed as the phrenic nerve stimulation is stable (i.e. while the phrenic nerve stimulation performed on the human patient is stable). In other words, the method for monitoring diaphragmatic response to phrenic nerve stimulation may comprise:

receiving in real-time a diaphragmatic compound motor action potential signal of a human patient;
computing a baseline value of a characteristic of the CMAP signal, the characteristic representing a diaphragmatic response intensity to phrenic nerve stimulation;
determining a threshold value of the characteristic, the threshold value representing a boundary of values of the characteristic indicative of upcoming diaphragmatic palsy, the determining of the threshold value including shifting the baseline value;
receiving in real-time an electrocardiogram signal of the human patient;
repeating in real-time and as the phrenic nerve stimulation is stable (i.e. during a period of time while the phrenic nerve stimulation is stable):
detecting a QRS complex in the ECG signal;
monitoring the CMAP signal;
computing a real-time value of the characteristic, the real-time value of the characteristic being asynchronous to the QRS complex;
comparing the real-time value to the threshold value; and
outputting an alert when the threshold is passed.

Thanks to such stability of the phrenic nerve stimulation, the method is not likely to output an alert due to instability of the phrenic nerve stimulation. As a result, the method is not likely to falsely detect an upcoming diaphragmatic palsy due to the real-time value of the characteristic changing because of such instability and thereby leading to a comparison that would have led to such an erroneous conclusion.

In an example, the phrenic nerve stimulation may comprise a series of electrical pulses delivered to the patient using one or more intravascular electrodes and/or one or more surface electrodes connected to an energy source that provides the energy for the electrical pulses. At each respective pulse, the phrenic nerve receives a respective electrical energy that results from the pulse. The stimulation may be stable such that over a given period of time, at each pulse during this period of time, the respective electrical energy received by the phrenic nerve for this pulse is equal to or larger than an electrical energy threshold (i.e. which is fixed, that is which is the same for all the pulses). The electrical energy threshold may be equal to or larger than a minimal electrical energy that is sufficient to cause a normal diaphragmatic response to phrenic nerve stimulation of the patient at rest (i.e. before cryoablation).

In other words, the method for monitoring diaphragmatic response to phrenic nerve stimulation may comprise, while a phrenic nerve stimulation is performed on a human patient (as part of the method or aside the method), the phrenic nerve stimulation comprising a series of electrical pulses delivered to the phrenic nerve using one or more intravascular electrodes and/or one or more surface electrodes connected to an energy source that provides the energy for the electrical pulses:

receiving in real-time a diaphragmatic compound motor action potential signal of the human patient;
computing a baseline value of a characteristic of the CMAP signal, the characteristic representing a diaphragmatic response intensity to the phrenic nerve stimulation;
determining a threshold value of the characteristic, the threshold value representing a boundary of values of the characteristic indicative of upcoming diaphragmatic palsy, the determining of the threshold value including shifting the baseline value;
receiving in real-time an electrocardiogram signal of the human patient;
during a given period of time, repeating in real-time and as the phrenic nerve stimulation is such that over said given period of time, at each pulse during this period of time, the respective electrical energy received by the phrenic nerve for this pulse is larger than the previously-discussed electrical energy threshold (in other words the phrenic nerve stimulation is stable up to said threshold):
detecting a QRS complex in the ECG signal;
monitoring the CMAP signal;

computing a real-time value of the characteristic, the real-time value of the characteristic being asynchronous to the QRS complex;
comparing the real-time value to the threshold value; and
outputting an alert when the threshold is passed.

In an example of the above-discussed example, the electrical energy threshold is equal to or larger than an electrical energy value that corresponds to (e.g. is equal to) a supramaximal stimulation energy. While the stimulation threshold of a nerve may be defined as the minimal energy to obtain the activation of a single axon, the stimulation threshold may vary within a nerve for different axons. The supramaximal response of the nerve is when all the axonal fibers of the nerve are activated. For the phrenic nerve, the supramaximal response yields the most important (i.e. largest) CMAP response/signal possible. The supramaximal stimulation energy corresponds in such an example to (e.g. is equal to) the electrical energy value that is necessary to obtain this most important CMAP response.

A method for monitoring diaphragmatic response to phrenic nerve stimulation has been discussed in detail.

In variations, the analyzing of the CMAP signal comprises analyzing, based on the received ECG signal or other data about the cardiac rhythm of the patient, the CMAP signal in any alternative manner, for example without computation of the baseline value, of the characteristic, and/or of the threshold value, and/or without comparison to the threshold value. The analysis of the CMAP signal may for example process the CMAP signal is any manner that takes into account (e.g. discards) portions of the CMAP signal synchronous to the QRS complex, for example by evaluating a global stability metric of stimulation based on the CMAP signal and/or by performing a coupled monitoring (e.g. a common display on a same screen) of the CMAP signal and of the ECG signal that detects these synchronous portions. The method may output an alert based on the analysis, upon detection of an upcoming palsy based on the analysis.

In variations, the method does not output an alert based on the CMAP analysis and/or detection of the threshold being passed. Instead, the method may process the CMAP signal and/or the result of the analysis in any manner, e.g. by automatically stopping a cryoablation upon upcoming palsy detection. Yet instead, the method may display the CMAP signal or the characteristic thereof and the threshold (e.g. simultaneously, for example in a superimposed manner), so that the practitioner performing a cryoablation sees them.

In variations, the threshold is not computed and there is no comparison of the real-time value to the threshold and no output of an alert. In such a case, the method may simply output the result of the analysis (e.g. a display of the CMAP signal or of the characteristic thereof) and the practitioner knows when to stop the cryoablation based on the output.

In variations, the method receives data about the cardiac rhythm of the human patient that is not the ECG signal. The method may receive other data, e.g. physiological data, about the cardiac rhythm of the human patient, instead of the ECG signal, this other data replacing the ECG signal in the previously discussed examples or variations.

The invention claimed is:

1. A computer-implemented method for monitoring diaphragmatic response to phrenic nerve stimulation, comprising:
receiving in real-time a diaphragmatic compound motor action potential (CMAP) signal of a human patient from a first plurality of electrodes;
computing a baseline value of a characteristic of the CMAP signal, the characteristic representing a diaphragmatic response intensity to phrenic nerve stimulation;
determining a threshold value of the characteristic, the threshold value representing a boundary of values of the characteristic indicative of upcoming diaphragmatic palsy, the determining of the threshold value including shifting the baseline value;
receiving in real-time an electrocardiogram (ECG) signal of the human patient from a second plurality of electrodes;
repeating in real-time:
detecting a QRS complex in the ECG signal;
monitoring the CMAP signal;
computing a real-time value of the characteristic, the real-time value of the characteristic being asynchronous to the QRS complex, the method computing the real-time value of the characteristic using only portions of the CMAP signal that correspond to the diaphragmatic response to phrenic nerve stimulations and that are not synchronous to any portion of the ECG signal that corresponds to a QRS complex occurrence, wherein, for computing the real-time value of the characteristic using only portions of the CMAP signal that correspond to the diaphragmatic response to the phrenic nerve stimulations and that are not synchronous to any portion of the ECG signal that corresponds to the QRS complex occurrence, the method comprises one or both of
discarding CMAP signal portions that correspond to diaphragmatic responses synchronous to detected QRS complexes, and
commanding phrenic nerve stimulation by triggering an occurrence of the phrenic nerve stimulation a predetermined amount of time after detection of an occurrence of the QRS complex such that a diaphragmatic response to the triggered occurrence of the phrenic nerve stimulation occurs and ends before a next occurrence of the QRS complex;
comparing the real-time value to the threshold value; and
outputting an alert when the threshold is passed.

2. The method of claim 1, wherein the real-time value of the characteristic is an average of the characteristic for several occurrences of the phrenic nerve stimulation.

3. The method of claim 2, wherein the real-time value of the characteristic is an average of the characteristic for a predetermined number of consecutive occurrences of the phrenic nerve stimulation.

4. The method of claim 3, wherein the predetermined number is below or equal to 5.

5. The method of claim 1, wherein the computing of the real-time value of the characteristic comprises calculating one or more CMAP measures performed each on a portion of the CMAP signal beginning at a predetermined amount of time after an occurrence of the phrenic nerve stimulation and lasting for a predetermined time duration after the occurrence of the phrenic nerve stimulation.

6. The method of claim 5, wherein:
the predetermined amount of time is larger than 3 ms and/or lower than 50 ms; and/or
the predetermined time duration is larger than 50 ms and/or lower than 150 ms.

7. The method of claim 1, wherein:
the characteristic is:
an amplitude difference between two consecutives peaks of the CMAP signal; or
an area between an isoelectric line and a portion of a curve representing two consecutives peaks of the CMAP signal; and/or
the threshold value corresponds to a drop of the baseline value which is larger than 25% and/or lower than 35%; and/or
the CMAP signal is received from one or more surface electrodes and/or one or more intravascular electrodes.

8. The method of claim 1, wherein the repeating in real-time of the detecting of the QRS complex in the ECG signal, of the monitoring of the CMAP signal, of the computing of the real-time value of the characteristic which is asynchronous to the QRS complex, of the comparing of the real-time value to the threshold value, and of the outputting of the alert when the threshold is passed, may be performed as the phrenic nerve stimulation is stable.

9. The method of claim 1, wherein the phrenic nerve stimulation comprises a series of electrical pulses delivered to the patient, the phrenic nerve receiving, at each respective pulse during a period of time, a respective electrical energy that results from the pulse, the respective electrical energy received by the phrenic nerve for the respective pulse being equal to or larger than an electrical energy threshold, the electrical energy threshold being equal to or larger than a minimal electrical energy that is sufficient to cause a diaphragmatic response to phrenic nerve stimulation of the patient at rest.

10. The method of claim 9, wherein the electrical energy threshold is equal to or larger than an electrical energy value that corresponds to a supramaximal stimulation energy.

11. A non-transitory computer-readable data storage medium having recorded thereon a computer program comprising instructions for performing a method for monitoring diaphragmatic response to phrenic nerve stimulation, comprising:
receiving in real-time a diaphragmatic compound motor action potential (CMAP) signal of a human patient;
computing a baseline value of a characteristic of the CMAP signal, the characteristic representing a diaphragmatic response intensity to phrenic nerve stimulation;
determining a threshold value of the characteristic, the threshold value representing a boundary of values of the characteristic indicative of upcoming diaphragmatic palsy, the determining of the threshold value including shifting the baseline value;
receiving in real-time an electrocardiogram (ECG) signal of the human patient;
repeating in real-time:
detecting a QRS complex in the ECG signal;
monitoring the CMAP signal;
computing a real-time value of the characteristic using only portions of the CMAP signal that correspond to the diaphragmatic response to the phrenic nerve stimulations and that are not synchronous to any portion of the ECG signal that corresponds to a QRS complex occurrence, the real-time value of the characteristic being asynchronous to the QRS complex, wherein computing the real-time value of the characteristic comprises one or both of:
discarding CMAP signal portions that correspond to diaphragmatic responses synchronous to detected QRS complexes, and
commanding phrenic nerve stimulation by triggering an occurrence of the phrenic nerve stimulation a predetermined amount of time after detection of an occurrence of the QRS complex such that a diaphragmatic response to the triggered occurrence of the phrenic nerve stimulation occurs and ends before a next occurrence of the QRS complex;
comparing the real-time value to the threshold value; and
outputting an alert when the threshold is passed.

12. A control unit comprising a processor coupled to a memory, the memory having recorded thereon a computer program comprising instructions for performing a method for monitoring diaphragmatic response to phrenic nerve stimulation, comprising:
receiving in real-time a diaphragmatic compound motor action potential (CMAP) signal of a human patient;
computing a baseline value of a characteristic of the CMAP signal, the characteristic representing a diaphragmatic response intensity to phrenic nerve stimulation;
determining a threshold value of the characteristic, the threshold value representing a boundary of values of the characteristic indicative of upcoming diaphragmatic palsy, the determining of the threshold value including shifting the baseline value;
receiving in real-time an electrocardiogram (ECG) signal of the human patient;
repeating in real-time:
detecting a QRS complex in the ECG signal;
monitoring the CMAP signal;
computing a real-time value of the characteristic using only portions of the CMAP signal that correspond to the diaphragmatic response to the phrenic nerve stimulations and that are not synchronous to any portion of the ECG signal that corresponds to a QRS complex occurrence, the real-time value of the characteristic being asynchronous to the QRS complex, wherein computing the real-time value of the characteristic comprises one or both of:
discarding CMAP signal portions that correspond to diaphragmatic responses synchronous to detected QRS complexes, and
commanding phrenic nerve stimulation by triggering an occurrence of the phrenic nerve stimulation a predetermined amount of time after detection of an occurrence of the QRS complex such that a diaphragmatic response to the triggered occurrence of the phrenic nerve stimulation occurs and ends before a next occurrence of the QRS complex;
comparing the real-time value to the threshold value; and
outputting an alert when the threshold is passed.

13. A system comprising:
a control unit comprising a processor coupled to a memory, the memory having recorded thereon a computer program comprising instructions for performing a method for monitoring diaphragmatic response to phrenic nerve stimulation, comprising:
receiving in real-time a diaphragmatic compound motor action potential (CMAP) signal of a human patient;

computing a baseline value of a characteristic of the CMAP signal, the characteristic representing a diaphragmatic response intensity to phrenic nerve stimulation;

determining a threshold value of the characteristic, the threshold value representing a boundary of values of the characteristic indicative of upcoming diaphragmatic palsy, the determining of the threshold value including shifting the baseline value;

receiving in real-time an electrocardiogram (ECG) signal of the human patient;

repeating in real-time:
    detecting a QRS complex in the ECG signal;
    monitoring the CMAP signal;
    computing a real-time value of the characteristic using only portions of the CMAP signal that correspond to the diaphragmatic response to the phrenic nerve stimulations and that are not synchronous to any portion of the ECG signal that corresponds to a QRS complex occurrence, the real-time value of the characteristic being asynchronous to the QRS complex, wherein computing the real-time value of the characteristic comprises one or both of:
        discarding CMAP signal portions that correspond to diaphragmatic responses synchronous to detected QRS complexes, and
    commanding phrenic nerve stimulation by triggering an occurrence of the phrenic nerve stimulation a predetermined amount of time after detection of an occurrence of the QRS complex such that a diaphragmatic response to the triggered occurrence of the phrenic nerve stimulation occurs and ends before a next occurrence of the QRS complex;
    comparing the real-time value to the threshold value; and
    outputting an alert when the threshold is passed, and:
a first plurality of electrodes configured to measure the CMAP signal,
a second plurality of electrodes configured to measure the ECG signal,
a phrenic nerve stimulation system, and/or
a cryoablation catheter.

14. The system of claim 13, wherein the first plurality of electrodes comprises one or more surface electrodes and/or one or more intravascular electrodes.

15. The system of claim 13, wherein the system further comprises:
a display for outputting a visual alert when the threshold is passed; and/or
a sound emitting device for outputting a sound alert when the threshold is passed.

* * * * *